US012667443B2

(12) United States Patent
Baltrunas et al.

(10) Patent No.: US 12,667,443 B2
(45) Date of Patent: Jun. 30, 2026

(54) ENDOVASCULAR ROBOTIC SYSTEM AND METHOD OF USE THEREOF

(71) Applicant: UAB Inovatyvi Medicina, Kaunas (LT)

(72) Inventors: Tomas Baltrunas, Kaunas (LT);
Evaldas Kalvaitis, Kaunas (LT);
Edvardas Satkauskas, Kaunas (LT);
Vilius Dambrauskas, Kaunas (LT);
Vaidas Labunskas, Kaunas (LT)

(73) Assignee: UAB Inovatyvi Medicina, Kaunas (LT)

( * ) Notice: Subject to any disclaimer, the term of this patent is extended or adjusted under 35 U.S.C. 154(b) by 921 days.

(21) Appl. No.: 17/759,837

(22) PCT Filed: Jan. 31, 2020

(86) PCT No.: PCT/EP2020/052419
§ 371 (c)(1),
(2) Date: Jul. 29, 2022

(87) PCT Pub. No.: WO2021/151502
PCT Pub. Date: Aug. 5, 2021

(65) Prior Publication Data
US 2023/0067021 A1     Mar. 2, 2023

(51) Int. Cl.
*A61B 34/37*          (2016.01)
*A61B 34/00*          (2016.01)
(Continued)

(52) U.S. Cl.
CPC ............. *A61B 34/76* (2016.02); *A61B 34/37* (2016.02); *A61B 2034/2055* (2016.02); *A61B 2034/301* (2016.02); *A61B 2034/303* (2016.02)

(58) Field of Classification Search
CPC ......... A61B 34/37; A61B 34/76; A61B 34/30; A61B 2090/064; A61B 2034/303;
(Continued)

(56) References Cited

U.S. PATENT DOCUMENTS

| | | | | |
|---|---|---|---|---|
| 5,078,714 A | 1/1992 | Katims | | |
| 6,728,599 B2 * | 4/2004 | Wang | ..................... | A61B 34/70 |
| | | | | 600/595 |

(Continued)

FOREIGN PATENT DOCUMENTS

| | | |
|---|---|---|
| CA | 2924153 | 9/2017 |
| DE | 100 53 976 | 5/2002 |

(Continued)

OTHER PUBLICATIONS

Naudin et al., A Robotic Platform for Endovascular Aneurysm Repair, 2019, IEEE, p. 996-1001 (Year: 2019).*
(Continued)

*Primary Examiner* — Mcdieunel Marc
(74) *Attorney, Agent, or Firm* — Levine Bagade Han LLP

(57) ABSTRACT

We describe an endovascular robotic system, comprising: a first endovascular robotic instrument located at a first location, and a second endovascular robotic instrument located at a second location. The first endovascular robotic instrument is communicatively coupled with the second endovascular robotic instrument. A first functioning of the first endovascular robotic instrument is identical to a second functioning of the second endovascular robotic instrument. The first endovascular robotic instrument comprises a first haptic feedback unit configured to generate first haptic feedback data dependent on a first movement, for implementing the first functioning, of the first endovascular robotic instrument. The first endovascular robotic instrument is configured to send the first haptic feedback data to the second endovascular robotic instrument. The second endovascular robotic instrument is configured to mimic, for implementing the second functioning, the first movement of the first endovascular robotic instrument based on the first haptic feedback data.

20 Claims, 6 Drawing Sheets

(51) Int. Cl.

*A61B 34/20*      (2016.01)

*A61B 34/30*      (2016.01)

(58) Field of Classification Search

CPC ........ A61B 2034/301; A61B 2034/743; A61B 90/361; A61B 34/74; A61B 2034/742; A61B 2034/744; A61B 2034/2055

See application file for complete search history.

(56)                  References Cited

U.S. PATENT DOCUMENTS

| 6,785,593 B2 * | 8/2004 | Wang | A61B 34/35 |
| | | | 606/1 |
| 6,799,088 B2 * | 9/2004 | Wang | A61B 34/35 |
| | | | 606/1 |
| 6,836,703 B2 * | 12/2004 | Wang | A61B 34/70 |
| | | | 600/595 |
| 8,390,438 B2 | 3/2013 | Olson et al. | |
| 2010/0114308 A1 * | 5/2010 | Maschke | A61F 2/2427 |
| | | | 623/2.37 |
| 2015/0173838 A1 | 6/2015 | Murphy et al. | |

FOREIGN PATENT DOCUMENTS

| WO | WO 2011/028627 | 3/2011 |
| WO | WO 2021/151502 | 8/2021 |

OTHER PUBLICATIONS

Abdelaziz et al., Toward a Versatile Robotic Platform for Fluoros-copy and MRI-Guided Endovascular Interventions: a Pre-Clinical Study, 2019, IEEE, p. 5411-5418 (Year: 2019).*

Rijanto et al., Trends in robot assisted endovascular catheterization technology: a review, 2017, IEEE, p. 34-41 (Year: 2017).*

Molinero et al., Haptic Guidance for Robot-Assisted Endovascular Procedures: Implementation and Evaluation on Surgical Simulator, 2019, IEEE, p. 5398-5403 (Year: 2019).*

* cited by examiner

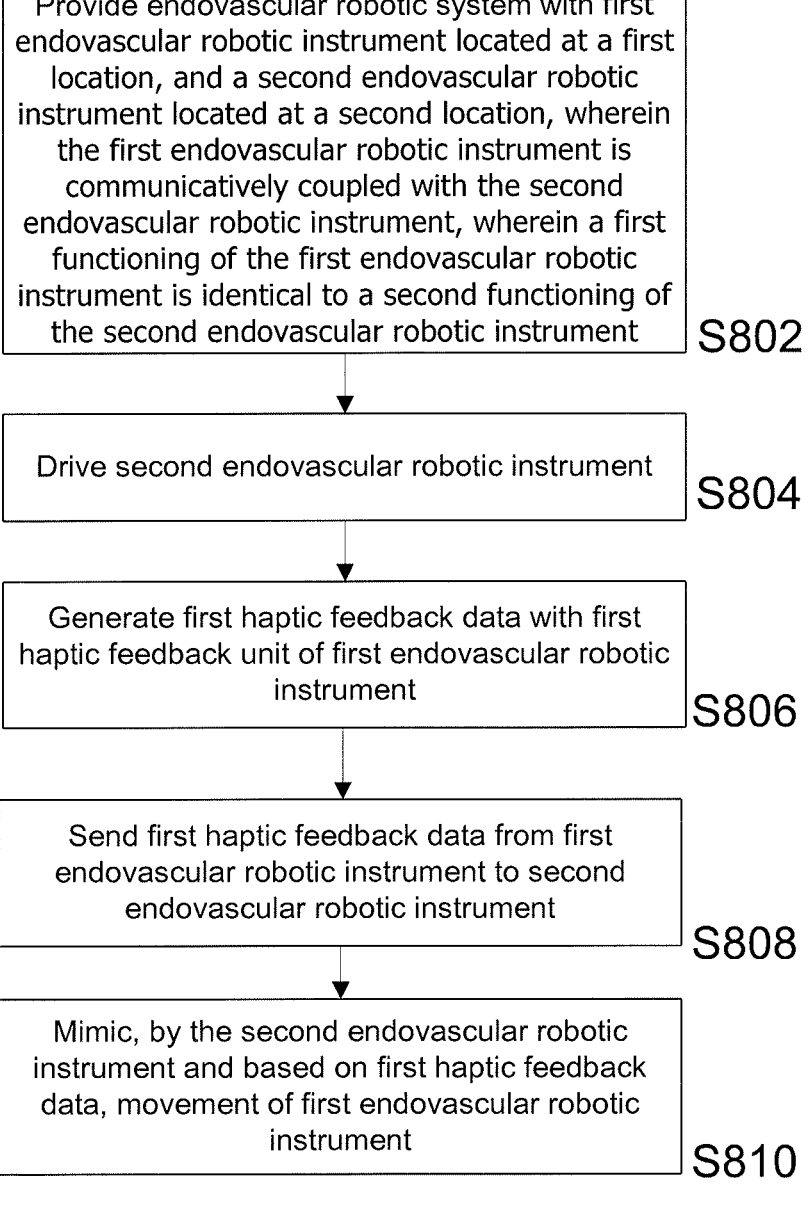

Provide endovascular robotic system with first endovascular robotic instrument located at a first location, and a second endovascular robotic instrument located at a second location, wherein the first endovascular robotic instrument is communicatively coupled with the second endovascular robotic instrument, wherein a first functioning of the first endovascular robotic instrument is identical to a second functioning of the second endovascular robotic instrument       S802

Drive second endovascular robotic instrument       S804

Generate first haptic feedback data with first haptic feedback unit of first endovascular robotic instrument       S806

Send first haptic feedback data from first endovascular robotic instrument to second endovascular robotic instrument       S808

Mimic, by the second endovascular robotic instrument and based on first haptic feedback data, movement of first endovascular robotic instrument       S810

800          Figure 8

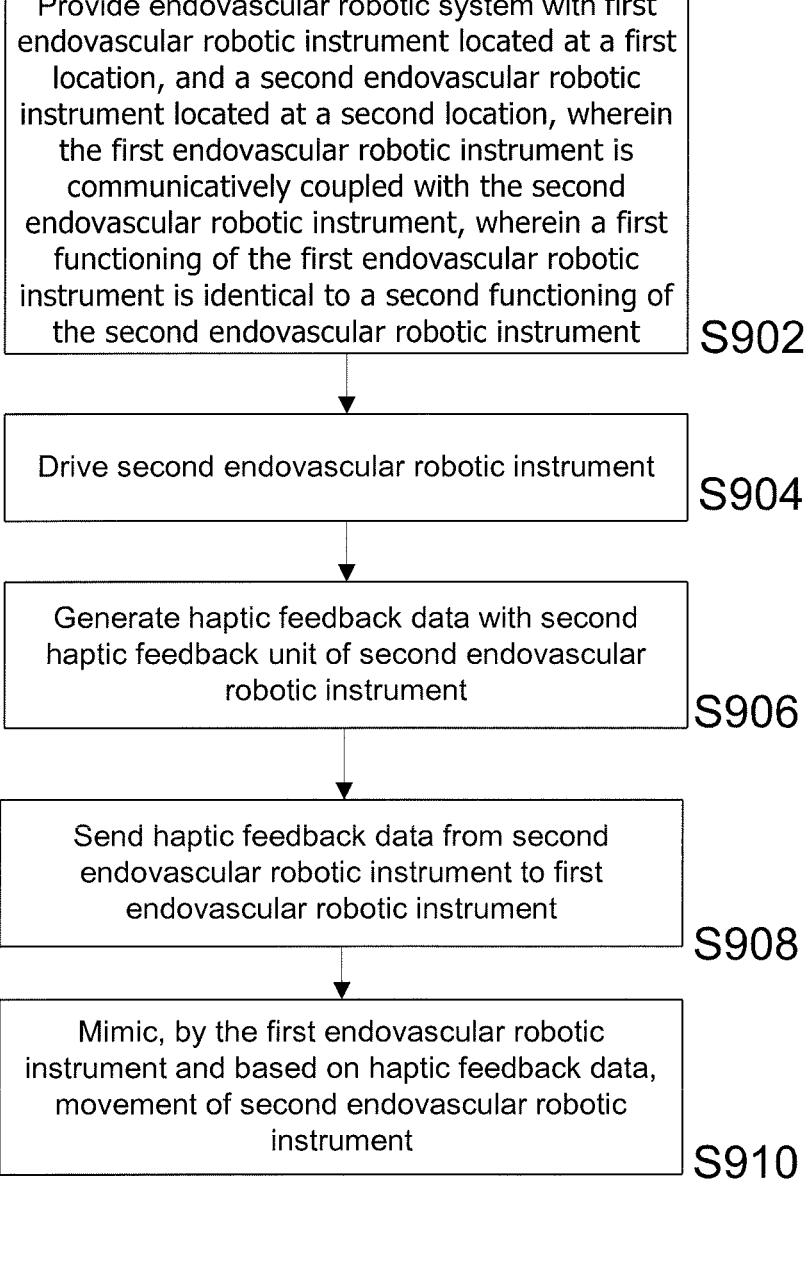

Provide endovascular robotic system with first endovascular robotic instrument located at a first location, and a second endovascular robotic instrument located at a second location, wherein the first endovascular robotic instrument is communicatively coupled with the second endovascular robotic instrument, wherein a first functioning of the first endovascular robotic instrument is identical to a second functioning of the second endovascular robotic instrument

S902

Drive second endovascular robotic instrument

S904

Generate haptic feedback data with second haptic feedback unit of second endovascular robotic instrument

S906

Send haptic feedback data from second endovascular robotic instrument to first endovascular robotic instrument

S908

Mimic, by the first endovascular robotic instrument and based on haptic feedback data, movement of second endovascular robotic instrument

ENDOVASCULAR ROBOTIC SYSTEM AND METHOD OF USE THEREOF

CROSS-REFERENCE TO RELATED APPLICATIONS

This application is a U.S. national phase under 35 U.S.C. 371 of International Patent Application Number PCT/EP2020/052419 filed Jan. 31, 2020, the content of which is incorporated herein by reference in its entirety.

FIELD OF THE INVENTION

The present invention generally relates to an endovascular robotic system and a method for using the endovascular robotic system in medical intervention, such as, for example, surgery.

BACKGROUND TO THE INVENTION

Endovascular specialists (for example (endo-)vascular surgeons, (interventional) cardiologists, (interventional) radiologists etc.) train, practice and develop intuitive skills to handle surgical tools. The mental imagery of skills of physicians also evolves by correlating their actions and responses of surgical tools within the human anatomy. An endovascular surgeon is generally guided by two senses: visual feedback from the imaging devices and reaction force feedback via the tool. Perception-actionvisualization abilities of surgeons are fine-tuned to a level where their surgical decisions are made even without observing their hand gestures.

Currently, existing robotic systems are focused exclusively on imaging feedback, but have ignored the other source of information: tactile feedback from surgical tools. Instrument controls using a joystick and a PC interface are closer to videogame controllers than control of surgical instruments and leave vascular surgeons with less feedback information which is available performing the procedure manually.

FIG. 1 shows a schematic illustration of a system according to the prior art. In this example, an endovascular specialist is standing near an X-ray beam generator and manipulates the (elongated) medical device. In some examples, the system may be operated by a technician and/or the endovascular specialists.

FIG. 2 shows a schematic illustration of a further system according to the prior art. In this example, a robot is controlled by a joystick, mouse (for example dedicated 3D mouse), keyboard or touchscreens.

Prior art can be found, for example, in U.S. Pat. No. 8,390,438 B2, which generally relates to a robotic catheter system including haptic feedback, in US 2015/0173838 A1, which generally relates to a variable drive force apparatus and method for a robotic catheter system, and in U.S. Pat. No. 5,078,714 A, which generally relates to a method and apparatus for placement of a probe in the body and the medical procedure for guiding and locating a catheter probe in the body.

The inventors have realized that existing vascular robotic systems are controlled via a computer interface, in contrast to what vascular surgeons are trained to do with, for example, guide wires and catheters.

There is therefore a need for improvements of (endo-)vascular robotic systems.

SUMMARY OF THE INVENTION

The invention is set out in the independent claim or claims. Preferred embodiments of the invention are outlined in the dependent claims.

In a first aspect according to the present disclosure, there is provided an endovascular robotic system, comprising: a first endovascular robotic instrument located at a first location, and a second endovascular robotic instrument located at a second location different from the first location, wherein the first endovascular robotic instrument is communicatively coupled with the second endovascular robotic instrument, wherein a first functioning of the first endovascular robotic instrument is identical (or similar) to a second functioning of the second endovascular robotic instrument, wherein the first endovascular robotic instrument comprises a first haptic feedback unit configured to generate first haptic feedback data dependent on a first movement, for implementing the first functioning, of the first endovascular robotic instrument, wherein the first endovascular robotic instrument is configured to send the first haptic feedback data to the second endovascular robotic instrument, and wherein the second endovascular robotic instrument is configured to mimic, for implementing the second functioning, the first movement of the first endovascular robotic instrument based on the first haptic feedback data received from the first endovascular robotic instrument.

The first and second locations may comprise first and second areas which are different from each other.

In some examples, the first endovascular robotic instrument may be used in order to treat or perform surgery on a patient who is located at the first location. The second endovascular robotic instrument may be controlled via the surgeon who is located at the second location.

Alternatively, the first endovascular robotic instrument may be controlled via the surgeon who is located at the first location. The second endovascular robotic instrument may be used in order to treat or perform surgery on a patient who is located at the second location.

The communicative coupling between the first endovascular robotic instrument and the second endovascular robotic instrument may be wired and/or wireless. A wireless communication may, for example, occur via one or more networks.

The first and second functioning may refer to respective purposes or tasks which may be performed using the first and second endovascular robotic instruments (or one or more components or parts of the first and second endovascular robotic instruments), respectively. The functioning may relate to a particular (type of) work or (type of) operation that is performed by or via the first and second endovascular robotic instruments, respectively. The functioning may relate to that of a (elongated) medical devices, such as but not limited to guide wire and/or a catheter and/or a stent and/or a percutaneous transluminal angioplasty balloon and/or a thrombectomy device and/or a coil and/or a glue system. In some examples, the first functioning and second functioning being identical may relate to a sensing functioning (using sensing parts and/or components of the instruments) and/or a driving functioning (using driving parts and/or components and/or gears of the instruments) being identical, while the hardware used for the sensing and/or driving may not necessarily be identical. In some examples, the sensing of forces may be identical for the two instruments, while the hardware may be different. Additionally or alternatively, the hardware of the first and second endovascular robotic instruments (or one or more components thereof) may be identical. In some examples, casing and/or mounting and/or sterility and/or software and/or user interface and/or firmware may be different (or identical).

The haptic feedback may, in some examples, relate to tactile feedback which may be obtained via the first haptic feedback unit.

Sending of the first haptic feedback data from the first endovascular robotic instrument to the second endovascular robotic instrument may be performed via a wired connection or coupling between the first endovascular robotic instrument and the second endovascular robotic instrument. Additionally or alternatively, the first endovascular robotic instrument may comprise a transmitter (or transceiver) and the second endovascular robotic instrument may comprise a receiver (or transceiver) such that the first haptic feedback data may be transmitted from the first endovascular robotic instrument to the second endovascular robotic instrument (partially or fully) over the air.

In some examples, the second endovascular robotic instrument comprises a drive unit which is configured to drive one or more components of the second endovascular robotic instrument so as for the second endovascular robotic instrument to mimic the first movement of the first endovascular robotic instrument based on the first haptic feedback data received from the first endovascular robotic instrument.

Example implementations according to the endovascular robotic system as described herein allow in particular to sense gestures of a surgeon, i.e. manipulations of the respective instrument and/or surgical actions, and provide natural (or close to natural) haptic (in particular tactile) feedback augmenting actions of the surgeon and ensuring adequate control of surgical instruments and tools.

The endovascular robotic system according to example implementations as described herein allow for controlling of an endovascular robotic instrument using real endovascular instruments. In some examples, a surgeon inserts the same or similar (i.e., for example having the same functioning) endovascular instrument or instruments as the one or ones which is/are inserted into the patient and/or be used during surgery of the patient at the same time. Haptic feedback is created to replicate the natural feeling of the endovascular instrument movement and resistance.

Example implementations according to the endovascular robotic system as described herein solve the (main) issues of existing robotic systems and opens up possibilities for safer, faster and more effective minimally invasive endovascular interventions.

An advantage of the endovascular robotic system according to example implementations as described herein in comparison to existing systems is haptic feedback and traditional control of all endovascular instruments using fine-tuned surgeons' perception-actionvisualization abilities. This provides for significant advantages in comparison to existing systems which use only visual feedback and control via, for example, a joystick.

The principle of example implementations according to the present disclosure can be used with all standard endovascular instruments and avoids the need of expensive instruments comprising, for example, (elongated) medical devices, such as, but not limited to catheters and/or guide wires and/or stents and/or percutaneous transluminal angioplasty balloons and/or thrombectomy devices and/or coils and/or glue systems, dedicated for the particular system.

In some examples of the endovascular robotic system, the second endovascular robotic instrument comprises a second haptic feedback unit configured to generate second haptic feedback data dependent on a second movement, for implementing the second functioning, of the second endovascular robotic instrument, wherein the second endovascular robotic instrument is configured to send the second haptic feedback data to the first endovascular robotic instrument, and wherein the first endovascular robotic instrument is configured to mimic, for implementing the first functioning, the second movement of the second endovascular robotic instrument based on the second haptic feedback data received from the second endovascular robotic instrument.

The haptic feedback may, in some examples, relate to tactile feedback which may be obtained via the second haptic feedback unit.

Sending of the second haptic feedback data from the second endovascular robotic instrument to the first endovascular robotic instrument may be performed via the wired connection or coupling between the first endovascular robotic instrument and the second endovascular robotic instrument. Additionally or alternatively, the second endovascular robotic instrument may comprise a transmitter (or transceiver) and the first endovascular robotic instrument may comprise a receiver (or transceiver) such that the second haptic feedback data may be transmitted from the second endovascular robotic instrument to the first endovascular robotic instrument (partially or fully) over the air.

In some examples, the first endovascular robotic instrument comprises a drive unit which is configured to drive one or more components of the first endovascular robotic instrument so as for the first endovascular robotic instrument to mimic the second movement of the second endovascular robotic instrument based on the second haptic feedback data received from the second endovascular robotic instrument.

Providing first and second haptic feedback units on the first and second endovascular robotic instruments, respectively, advantageously allow for sensing gestures of a surgeon and providing natural (or close to natural) haptic (in particular tactile) feedback augmenting actions of the surgeon and ensuring adequate control of surgical instruments and tools.

At the same time, further haptic feedback may be obtained via the haptic feedback unit arranged at the endovascular robotic instrument arranged where the patient is treated, based on which the surgeon can, for example, feel the resistance from parts of the patient undergoing surgery. This may allow for improving precision when performing surgery on the patient, as the surgeon can more finely feel the resistance from those parts of the patient on which surgery is performed. At the same time, forces applied by the surgeon to the endovascular robotic instrument he/she operates physically (i.e. directly) may be applied to the endovascular robotic instrument with which surgery is performed on the patient in real time.

In some examples of the endovascular robotic system, the first endovascular robotic instrument comprises one or more first endovascular robotic instrument components, wherein the second endovascular robotic instrument comprises one or more second endovascular robotic instrument components, and wherein one of said first endovascular robotic instrument components is identical (for example identical in functioning and/or identical in terms of the hardware and/or software used for performing such functioning) to a corresponding, respective one of said second endovascular robotic instrument components. In some examples, one of the first endovascular robotic instrument components is identical to a corresponding, respective one of the second endovascular robotic instrument components. In some examples, some or all of the first endovascular robotic instrument components are identical to corresponding, respective ones of the second endovascular robotic instrument components. Providing components of the first endovascular robotic instrument and the second endovascular robotic instrument which are identical to each other allows for particularly precise surgery due to improved precision based on haptic feedback obtained via one of the endovascular robotic instruments and used for driving components of the other one of the endovascular robotic instruments using identical components having identical characteristics, such as but not limited to physical properties (for example shape (of, for example, a diagnostic catheter) and/or weight and/or sensing and/or driving precision and/or driving speed and/or driving torquability and/or driving pushability and/or support characteristics) of the component(s) of the endovascular robotic instruments.

In some examples of the endovascular robotic system, said mimicking of a said movement of a said endovascular robotic instrument comprises driving a said endovascular robotic instrument component. A drive unit may be provided on the second endovascular robotic instrument (and, in some examples, additionally on the first endovascular robotic instrument) via which one or more (and in particular all) of the components of the second endovascular robotic instrument (and, in some examples, of the first endovascular robotic instrument) may be driven based on the first haptic feedback data (and, in some examples, based on the second haptic feedback data).

In some examples of the endovascular robotic system, the first endovascular robotic instrument comprises a first (elongated) medical device such as but not limited to catheter and/or a first guide wire and/or a first stent and/or a first percutaneous transluminal angioplasty balloon and/or a first thrombectomy device and/or a first coil and/or a first glue system. Additionally or alternatively, the second endovascular robotic instrument comprises a second (elongated) medical device such as but not limited to catheter and/or a second guide wire and/or a second stent and/or a sec—and percutaneous transluminal angioplasty balloon and/or a second thrombectomy device and/or a second coil and/or a second glue system.

In some examples, the endovascular robotic system further comprises: an optical detection unit arranged at the first location, and a visualization unit arranged at the second location, wherein the optical detection unit is configured to optically detect said first movement, generate, based on said optical detection of said first movement, movement data and send said movement data to the visualization unit, and wherein the visualization unit is configured to visualize, based on the movement data, said first movement. This may advantageously allow, in particular, for the surgeon to see movement of the first endovascular robotic instrument, and, in some examples, additionally parts of the body of the patient on which surgery is performed and/or with which the first endovascular robotic instrument interacts. Surgery may hereby be performed more precisely based not only on the natural (or close to natural) feeling due to haptic feedback, but also based on visualization of the first movement of the first endovascular robotic instrument.

In some examples of the endovascular robotic system, the visualization unit is configured to visualize at least a part of the first endovascular robotic instrument as a virtual extension of at least a part of the second endovascular robotic instrument. In some examples, the entire first endovascular robotic instrument may be visualized by the visualization unit. Visualizing on the visualization unit at least a part of the first endovascular robotic instrument as a virtual extension of at least a part of the second endovascular robotic instrument allows, in particular with the haptic feedback, for a very natural feeling in particular when the surgeon, located at the second location, performs surgery on the patient located at the first location, thereby improving surgeon experience and precision of surgery.

In some examples of the endovascular robotic system, the first haptic feedback unit comprises a first linear force sensor configured to sense a first linear force acting on the first endovascular robotic instrument and/or a first rotational force sensor configured to sense a first rotational force acting on the first endovascular robotic instrument. Additionally or alternatively, in some examples of the endovascular robotic system, the second haptic feedback unit comprises a second linear force sensor configured to sense a second linear force acting on the second endovascular robotic instrument and/or a second rotational force sensor configured to sense a second rotational force acting on the second endovascular robotic instrument. Providing a combination of a linear force sensor and a rotational force sensor may advantageously allow for precisely obtaining haptic feedback data. The combination of linear force sensing and rotational force sensing may be implemented in a single sensor in example implementations and embodiments outlined throughout the present disclosure.

In some examples, the endovascular robotic system is configured to: determine a relative force between (i) the first linear force and the second linear force, and/or (ii) the first rotational force and the second rotational force, and drive the first endovascular robotic instrument and/or the second endovascular robotic instrument to (i) adjust the first linear force to be equal to the second linear force and/or adjust the second linear force to be equal to the first linear force, and/or (ii) adjust the first rotational force to be equal to the second rotational force and/or adjust the second rotational force to be equal to the first rotational force. Adjusting the relative force between forces advantageously allows for driving one or both of the endovascular robotic instruments so as to improve mimicking movements of one of the endovascular robotic instruments by the other one of the endovascular robotic instruments.

In some examples, respective forces may not be adjusted to be equal, but may be adjusted to deviate from each other only by a predefined threshold. Additionally or alternatively, respective forces may be adjusted such that one force may be higher than the corresponding, respective force by a predefined factor.

In some examples, the endovascular robotic system is further configured to determine, based on sensor readings of the first system force sensor and the second system force sensor, whether to adjust the first system force to be equal to the second system force and/or adjust the second system force to be equal to the first system force. Example implementations of the endovascular robotic system therefore allow for changing roles of the master endovascular robotic instrument and slave endovascular robotic instrument interchangeably in real time. This may in particular allow for faster mimicking of movements of the first endovascular robotic instrument by the second endovascular robotic instrument, and vice versa. In some examples, respective forces may not be adjusted to be equal, but may be adjusted to deviate from each other only by a predefined threshold. Additionally or alternatively, respective forces may be adjusted such that one force may be higher than the corresponding, respective force by a predefined factor.

In some examples of the endovascular robotic system, a said sensor is configured to: move linearly and/or rotationally together with a corresponding, respective said endovascular robotic instrument, and create an increased and/or decreased force to said corresponding, respective endovascular robotic instrument during said linear and/or rotational movement together with said corresponding, respective endovascular robotic instrument. Forces may hence be applied to the respective endovascular robotic instrument in a precise manner based on respective haptic feedback data.

In some examples of the endovascular robotic system, the first endovascular robotic instrument comprises first rotational and axial motor gears for driving the first endovascular robotic instrument axially and rotationally, wherein the second endovascular robotic instrument comprises second rotational and axial motor gears for driving the second endovascular robotic instrument axially and rotationally, and wherein the first rotational and axial motor gears are identical to the second rotational and axial motor gears (or the first rotational and axial motor gears are similar to the second rotational and axial motor gears insofar that the respective rotational and axial motor gears do not deviate from each other by more than a predefined threshold in terms of forces, and hence acceleration, they can apply for driving the respective endovascular robotic instrument). Driving the first and second endovascular robotic instruments using the same driving units further improves precision for mimicking movement of one of the endovascular robotic instruments by the other one of the endovascular robotic instruments and/or for adjusting axial and/or rotational forces acting on the respective endovascular robotic instruments with respect to each other.

In some examples, the endovascular robotic system further comprises a data store adapted to store said (first and/or second) haptic feedback data. The haptic feedback data may hence, for example, be analyzed subsequently to using the endovascular robotic system for surgery. In some examples, haptic feedback data may be used to fine-tune further versions of the system. Additionally or alternatively, haptic feedback data may be used to create a learning console for residents and/or doctors, allowing for virtual testing of new devices. Additionally or alternatively, haptic feedback data may be used to train residents and/or doctors and/or artificial intelligence, AI, and perform certain steps/procedures automatically.

In some examples, the data store may be adapted to store the haptic feedback data together with (or without) visual data obtained via another medical instrument, such as an X-ray detector.

In some examples, the endovascular robotic system is further configured to: retrieve said haptic feedback data from the data store, and drive the first endovascular robot—is instrument to perform said first functioning and/or drive the second endovascular robotic instrument to perform said second functioning. This may allow, for example, for using haptic feedback data for training purposes of surgeons and/or for performing the same procedure based on precisely defined operating parameters of the respective endovascular robotic instruments.

In some examples of the endovascular robotic system, the communicative coupling of the first endovascular robotic instrument with the second endovascular robotic instrument comprises a wireless communicative coupling.

In some examples, the endovascular robotic system further comprises one or more controls, in particular comprising one or more touch screens and/or one or more monitors, wherein the one or more controls are configured to indicate a status of the endovascular robotic system (for example one or both of the first and second endovascular robotic instruments) and output a (for example optical and/or acoustic) signal dependent on the status of the endovascular robotic system. In some examples, the status comprises a value of a force applied to one or both of the first and second endovascular robotic instruments, wherein a (for example optical and/or acoustic and/or vibration) signal is output if the force is above (or below) a threshold force. Additionally or alternatively, the signal indicates when replacing of a component of an endovascular robotic instrument (for example a different (elongated) medical device) is required.

We further describe a (first) method comprising: providing an endovascular robotic system generally as described herein according to one or more example implementations (and in particular according to any one of the appended claims); driving the second endovascular robotic instrument (for example by a surgeon); generating, by the first endovascular robotic instrument, first haptic feedback data (based on the first endovascular robotic instrument mimicking movement of the second endovascular robotic instrument); sending, by the first endovascular robotic instrument, the first feedback data to the second endovascular robotic instrument; and mimicking, by the second endovascular robotic instrument and based on the first haptic feedback data, movement of the first endovascular robotic instrument.

We further describe a (second) method comprising: providing an endovascular robotic system generally as described herein according to example implementations (and in particular according to any one of the appended claims); driving the second endovascular robotic instrument (for example by a surgeon); generating, by the second endovascular robotic instrument, haptic feedback data; sending, by the second endovascular robotic instrument, the feedback data to the first endovascular robotic instrument; and mimicking, by the first endovascular robotic instrument and based on the haptic feedback data, movement of the second endovascular robotic instrument.

The first and second methods described above may be combined.

We further describe a method for performing surgery on a patient using the endovascular robotic instrument according to any one of the example implementations as described herein, in particular using one or both of the first and second methods described above.

We further describe a medical intervention system, comprising: a first medical instrument located at a first location, and a second medical instrument located at a second location different from the first location, wherein the first medical instrument is communicatively coupled with the second medical instrument, wherein the first medical instrument is configured to perform a first type of intervention on a patient, wherein the second medical instrument is configured to perform a second type of intervention on a patient, wherein the first type and the second type are identical or substantially identical types of intervention, wherein the first medical instrument comprises a first haptic feedback unit configured to generate first haptic feedback data dependent on a first movement of the first medical instrument, wherein the first medical instrument is configured to send the first haptic feedback data to the second medical instrument, and wherein the second medical instrument is configured to mimic the first movement of the first medical instrument based on the first haptic feedback data received from the first medical instrument.

The medical intervention system may comprise one or more of the features and components of the endovascular robotic system as described above and below throughout the present disclosure.

We further describe a medical intervention system, comprising: a first medical instrument for intervention on a patient, wherein the first medical instrument is located at a first location, and a second medical instrument for intervention on a said patient, wherein the second medical instrument is located at a second location different from the first location, wherein the first medical instrument is communicatively coupled with the second medical instrument, and wherein the medical intervention system is configured to trigger movement of the second medical instrument upon movement of the first medical instrument. In some examples, the movement of the second medical instrument comprises a movement to mimic said movement of the first medical instrument.

The medical intervention system may comprise one or more of the features and components of the endovascular robotic system as described above and below throughout the present disclosure.

We further describe a method for intervention on a patient, the method comprising: providing an endovascular robotic system or a medical intervention system according to any one or more of the example implementations as described herein; operating the second endovascular robotic instrument or the second medical instrument, respectively; and triggering movement of the first endovascular robotic instrument or the first medical instrument, respectively, to mimic said operating of the second endovascular robotic instrument or the second medical instrument, respectively.

Throughout the present disclosure, mimicking of movement of an endovascular robotic instrument by another endovascular robotic instrument may comprise driving one or both endovascular robotic instruments so that the same force of forces (or one force is larger than another force by a predefined factor) act on both endovascular robotic instruments.

Furthermore, throughout the present disclosure, any references regarding an intervention may comprise, for example, surgery.

BRIEF DESCRIPTION OF THE DRAWINGS

These and other aspects of the invention will now be further described, by way of example only, with reference to the accompanying figures, wherein like reference numerals refer to like parts, and in which:

FIG. 8 shows a flow diagram of a method according to some example implementations as described herein; and FIG. 9 shows a flow diagram of a method according to some example implementations as described herein.

DETAILED DESCRIPTION OF PREFERRED EMBODIMENTS

The present disclosure generally relates to an endovascular robotic solution. Systems and methods according to example implementations as described herein may be used in the field of elongated medical devices such as but not limited to guide wire and/or catheter systems for performing therapeutic procedures and, in particular, to an endovascular procedure method and principle for navigating elongated medical devices such as but not limited to guide wire and/or catheter with haptic feedback. The system outlined above and in the following examples may additionally or alternative use various (elongated) medical devices such as but not limited to stents and/or percutaneous transluminal angioplasty balloons and/or thrombectomy devices and/or coils and/or glue systems.

Figure 1:
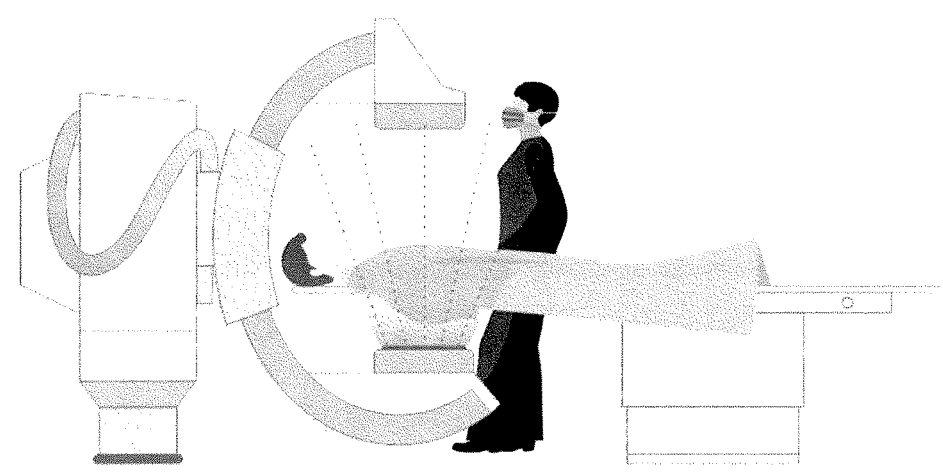
FIG. 1 shows a schematic illustration of a system according to the prior art.
Figure 2:
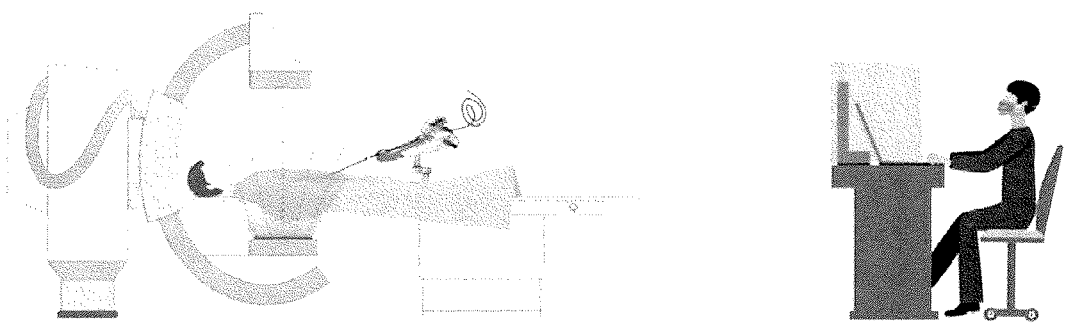
FIG. 2 shows a schematic illustration of a system according to the prior art.
Figure 3:
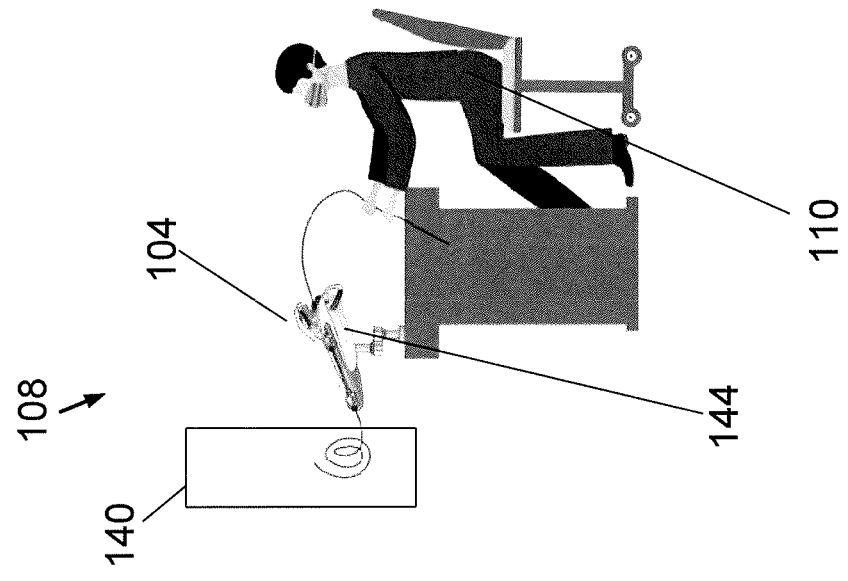
FIG. 3 shows a schematic illustration of an endovascular robotic system according to some example implementations as described herein.
Figure 3:
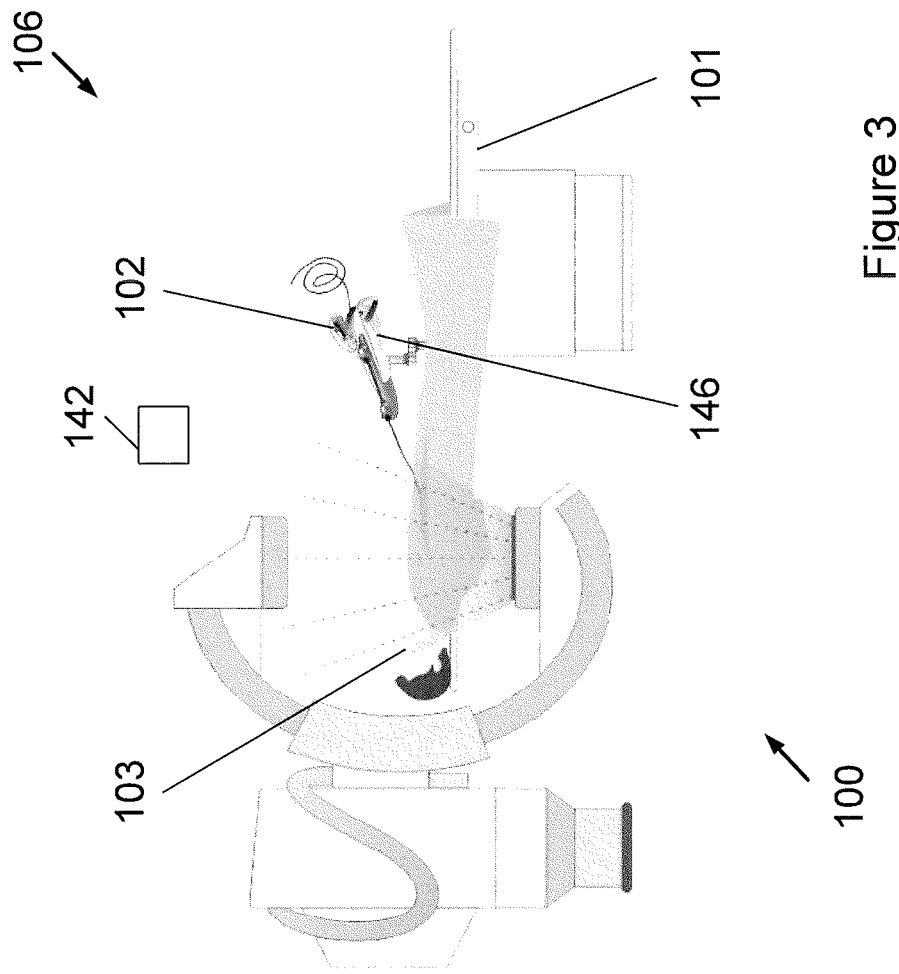

FIG. 3 shows a schematic illustration of an endovascular robotic system 100 according to some example implementations as described herein.

In this example, a patient 103 is lying on a table 101. The patient 103 undergoes surgery with the endovascular robotic instrument 102.

In this example, the endovascular robotic system 100 further comprises an optical detection unit 142 which is configured to optically detect movement of the endovascular robotic instrument 102 and also parts of the patient 103 on which surgery is performed via the endovascular robotic instrument 102.

The endovascular robotic instrument 102 comprises, in this example, rotational and axial motor gears 146 via which the endovascular robotic instrument 102 may be driven axially and rotationally. The rotational and axial motor gears 146 may be used in order to drive individual components of the endovascular robotic instrument 102, in particular the guide wire and the catheter of the endovascular robotic instrument 102.

The endovascular robotic instrument 102 and the optical detection unit 142 are arranged at a first location 106 which is different from a second location 108 at which the surgeon 110 operates.

In this example, a second endovascular robotic instrument 104 is arranged at the second location 108, whereby the surgeon 110 controls the endovascular robotic instrument 104.

In this example, the second endovascular robotic instrument 104 is identical to the first endovascular robotic instrument 102. In some other examples, however, the second endovascular robotic instrument 104 is similar (that is, at least identical in its functioning) to the first endovascular robotic instrument 102.

In this example, the endovascular robotic instrument 104 comprises rotational and axial motor gears 144 via which the second endovascular robotic instrument 104 may be driven axially and rotationally. The rotational axial motor gears 144 may be used in order to drive individual components of the second endovascular robotic instrument 104, in particular the guide wire and the catheter of the endovascular robotic instrument 104.

In this example, the endovascular robotic system 100 further comprises a visualization unit 140 arranged at the second location 108. The optical detection unit 142 is configured to optically detect movement of the first endovascular robotic instrument 102 (and parts of the patient on which surgery via the first endovascular robotic instrument 102 is performed), generate, based on the optical detection of said movement, movement data and send the movement data to the visualization unit 140. The visualization unit 140 is configured to visualize, based on the movement data, the movement of the first endovascular robotic instrument 102 (and parts of the patient 103 on which surgery is performed via the first endovascular robotic instrument 102).

The surgeon may manipulate (for example a catheter and/or a guide wire of) the second endovascular robotic instrument 104, wherein this movement is mimicked by the first endovascular robotic instrument 102 so as to reach the required areas of the patient body. The surgeon may get a haptic feedback of the first endovascular robotic instrument 102 when it crosses or hits particular areas of the patient body.

The endovascular robotic system consists of two modules (endovascular robotic instruments) with linear and rotational force sensors (in some examples, the linear force sensing and rotational force sensing is provided for via a single (integrated) sensor) capable of sensing surgical actions in providing adequate haptic (in particular tactile) feedback for rotational and linear movement of a guide wire and catheter.

Example implementations of the present disclosure provide for sensors and a system which allow a surgeon to have a haptic feedback of the catheter and/or guide wire being remote from the patient. The sensors may use an auto balance principle: relative forces at both ends of the catheter and guide wire may be sensed and the same forces may be reproduced at another end (i.e. another endovascular robotic instrument) by the drive system. Master and slave modules may have the same sensor systems installed for linear and rotational movements with no or minimum or com-pensated friction and can therefore be manipulated with no/very little additional resistance caused by the system. The system therefore allows a surgeon to control the endovascular robotic instrument using passive surgical tools with close to natural tactile perception.

In some examples, the same forces acting on one of the endovascular robotic instruments may be reproduced at the other one of the endovascular robotic instruments. In some examples, forces acting on one of the endovascular robotic instruments may be reproduced similarly at the other one of the endovascular robotic instruments. In some examples, forces acting on one of the endovascular robotic instruments may be tuned up (or lowered) based on a predefined factor at the other one of the endovascular robotic instruments based on the operator's preferences.

Master and slave modules (i.e. endovascular robotic instruments or particular one or more components thereof) may change the role from being master to slave and vice versa at real time, depending on sensor readings of the sensors of the modules and force balance between forces acting on the respective sensors.

Figure 4:
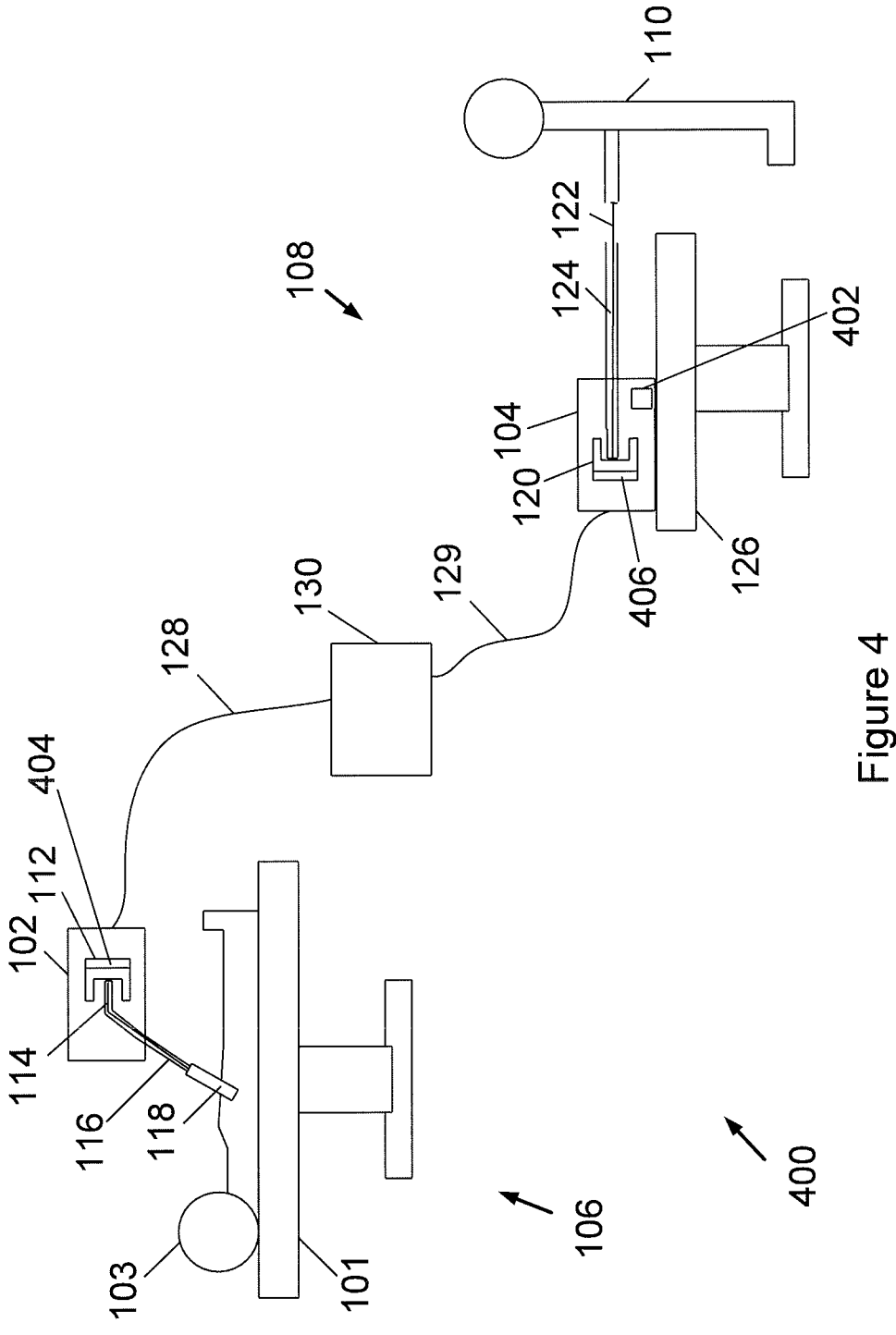
FIG. 4 shows a further schematic illustration of an endovascular robotic system according to some example implementations as described herein.

FIG. 4 shows a further schematic illustration of the endovascular robotic system 400 according to some example implementations as described herein.

In this example, the first endovascular robotic instrument 102 comprises a catheter 116 comprising an introducer catheter 118.

The first endovascular robotic instrument 102 further comprises, in this example, a guide wire 114 which is coupled to a sensor 112. The sensor 112 is configured to detect axial and rotational forces acting on the sensor 112 via the guide wire 114. Sensor detected and (or) created forces 404 may be used in order to generate haptic feedback data. Throughout examples of the present disclosure, a sensor may, additionally or alternatively to sensing forcing, create a (predefined) force (or forces) in particular to generate a certain (feeling of) resistance.

In this example, the first endovascular robotic instrument 102 is coupled via a wire 128 to a controller 130 which is used for controlling communications between the first endovascular robotic instrument 102 and the second endovascular robotic instrument 104. In particular, the controller 130 is configured to provide haptic feedback data from the first endovascular robotic instrument 102 to the second endovascular robotic instrument 104 and vice versa. The second endovascular robotic instrument 104 is, in this example, coupled to the controller 130 via wire 129.

In some examples, one or both of the first endovascular robotic instrument 102 and the second endovascular robotic instrument 104 are coupled to the controller 130 wirelessly. A direct wired or wireless communication path (without a controller along the communication path) between the first endovascular robotic instrument 102 and the second endovascular robotic instrument 104 may be provided in some examples.

In this example, the surgeon 110 is operating the second endovascular robotic instrument 104 arranged at the second location 108. In this example, the surgeon 110 operates the catheter 124 via guide wire 122.

The second endovascular robotic instrument 104 comprises a sensor 120 which is configured to detect axial and rotational forces acting on the sensor 120. Sensor detected and (or) created forces 406 may be used in order to generate haptic feedback data.

In this example, the second endovascular robotic instrument 104 is arranged on a table 126.

The second endovascular robotic instrument 104 comprises, in this example, a data store 402 which is adapted to store haptic feedback data. In this example, the data store 402 is adapted to store haptic feedback data generated via one or both of the sensor 112 and the sensor 120. As will be appreciated, the data store 402 may be arranged in the first endovascular robotic instrument 102. Alternatively, the data store 402 may be arranged at a location which is different from the first location 106 and the second location 108. As will be appreciated, components of the data store 402 may be arranged at different locations, including but not necessarily limited to the first location 106 and the second location 108. Haptic (for example tactile) feedback data can be stored in the data store 402 and may later be used for training purposes of the surgeon.

As outlined above, the surgeon 110 is not located in the main operating theatre (next room, or even another place or country; in some instances, the two instruments may be located in the same room), and manipulates catheter 124 (exactly the same (or similar) as the one used on/in the patient 103) and guide wire 122 (exactly the same (or similar) as the one used on/in the patient 103) and has the same tactile (reaction force) (or generally haptic) feedback from the catheter and guide wire as if he/she stands next to the patient 103 in the operating theatre.

The same (or similar) robotic guidance (rotation and axial rotation motor gears) and sensing systems may be provided in the first endovascular robotic instrument 102 and the second endovascular robotic instrument 104, respectively, which communi-cate with each other via cable (or wireless) communication channel 128/129 and through the controller 130.

While elongated medical devices are shown (where one medical device may fully or partially be inside the other medical device), it will be appreciated that the medical device or devices may have other shapes as those shown and described in the present disclosure.

The endovascular robotic system 400 comprises, in some examples, an optical detection unit at location 106 and a visualization unit at location 108, as is outlined above in relation to the endovascular robotic system 100 shown in FIG. 3.

Figures 5, 6, 7:
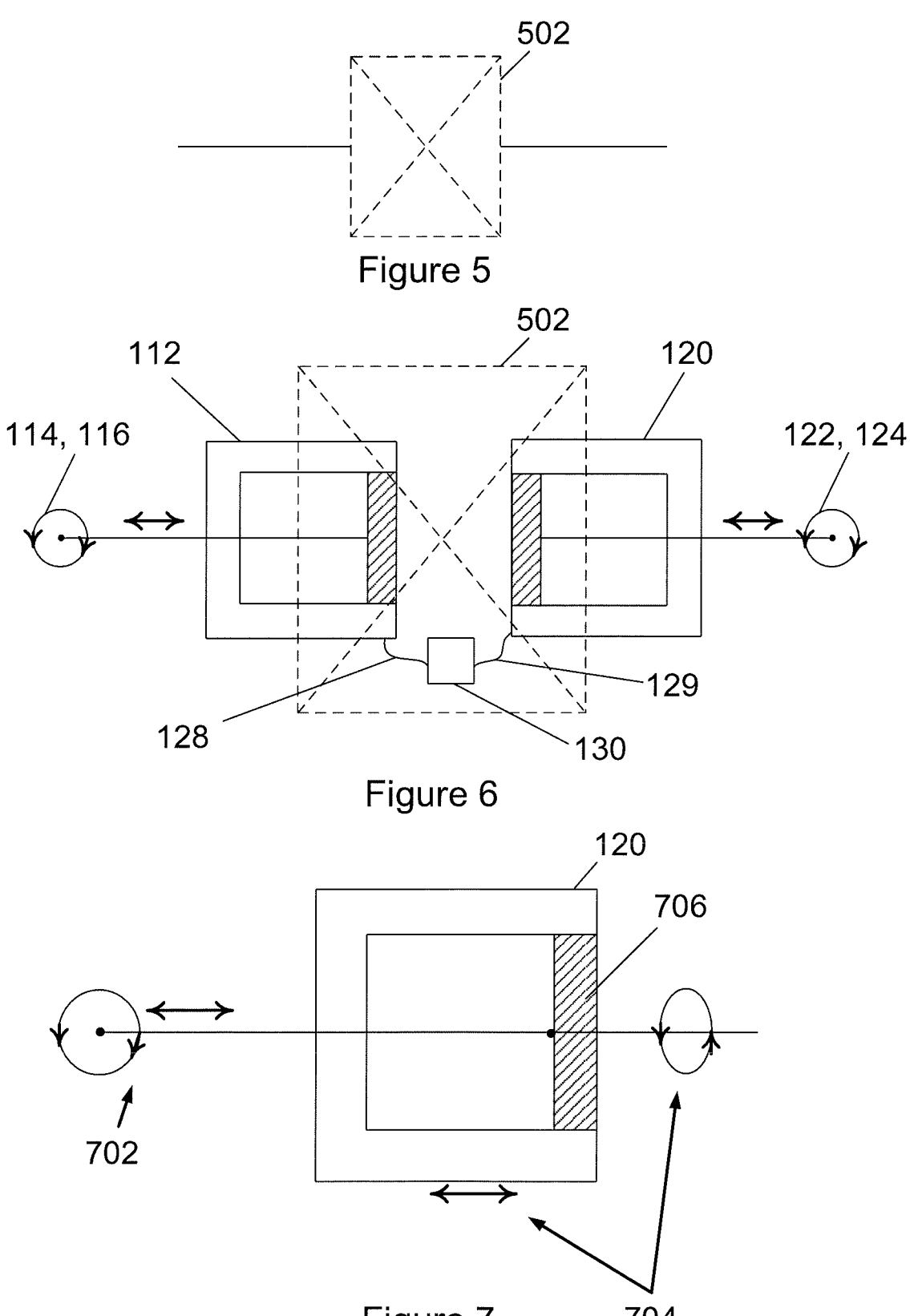
FIG. 5 shows a schematic illustration of a virtual cut according to some example implementations as described herein.
FIG. 6 shows a schematic illustration of a virtual cut and sensors according to some example implementations as described herein.
FIG. 7 shows a schematic illustration of a sensor according to some example implementations as described herein.

FIG. 5 shows a schematic illustration of a virtual cut 502 according to some example implementations as described herein.

The first endovascular robotic instrument 102 and the second endovascular robotic instrument 104 are connected together, which provides tactile or (generally) haptic feedback for the surgeon, but having only a virtual connection between the guide wire and catheter ends in the surgeon hands and in the patient.

In the virtual cut of the endovascular robotic instruments, for instance, the wire may be inserted into the patient and the surgeon may sit in the other room (or generally other location) and feels as if he were to insert the same wire with on-time resistance into the patient.

In FIG. 5, the catheters 116 and 124 (and/or the guide wires 114 and 122) are shown as being virtually cut. At the place of this cut, there is the communication line (wireless or wired based on wires 128 and 129), and the controller 130 is configured to make a virtual connection between the catheter 116 and the catheter 124 (and/or the guide wire 114 and the guide wire 122), providing with the haptic feedback a feeling, as if the catheter and/or the guide wire are continuous.

FIG. 6 shows a schematic illustration of a virtual cut and sensors according to some example implementations as described herein.

The catheter 116 and/or the guide wire 114 can, in this example, move in two directions: linearly (in the front and backwards direction) and rotationally (in a clockwise and/or counterclockwise direction). Similarly, the catheter 124 and/or the guide wire 122 can, in this example, move in two directions: linearly (in the front and backwards direction) and rotationally (in a clockwise and/or counterclockwise direction).

FIG. 7 shows a schematic illustration of a sensor 120 and forces sensing according to some example implementations as described herein.

In this example, sensor 120 detects linear and rotational forces of the catheter or guide wire in real time on one end. The sensor 120 can move linearly and rotationally together with the catheter and guide wire and, at the same time, the sensor 120 can detect and create more or less force 706 to the catheter or guide wire. This may equally be applied to the sensor 112.

For a complete system, two sensors which are identical to each other (or at least similar, that is identical in functioning, to each other) are used (one in the first endovascular robotic instrument 102 and one in the second endovascular robotic instrument 104). These sensors interact together in real time to detect the relative force in one and duplicate that size of the force at the other endovascular robotic instrument (via a driving unit), and vice versa. In this way, haptic feedback and feeling/sense of continuously connected catheter and/or guide wire can be created.

FIG. 8 shows a flow diagram of a method 800 according to some example implementations as described herein.

At step S802, the method 800 comprises providing an endovascular robotic system according to any one of the example implementations as described herein. In this example, the endovascular robotic system comprises a first endovascular robotic instrument located at the first location and a second endovascular robotic instrument located at a second location which is different from the first location. The first endovascular robotic instrument is communicatively coupled with the second endovascular robotic instrument, wherein a first functioning of the first endovascular robotic instrument is identical to a second functioning of the second endovascular robotic instrument.

At step S804, the method 800 comprises driving the second endovascular robotic instrument. Driving the second endovascular robotic instrument may be performed by the surgeon who is located at the second location.

At step S806, first haptic feedback data is generated with a first haptic feedback unit of the first endovascular robotic instrument. The first haptic feedback data is generated, in some examples, using a sensor which may sense axial and/or rotational forces.

At step S808, the first haptic feedback data is sent from the first endovascular robotic instrument to the second endovascular robotic instrument.

At step S810 of the method 800, movement of the first endovascular robotic instrument is mimicked by the second endovascular robotic instrument based on the first haptic feedback data received from the first endovascular robotic instrument.

FIG. 9 shows a flow diagram of a method 900 according to some example implementations as described herein.

At step S902, the method 900 comprises providing an endovascular robotic system according to any one of the example implementations as described herein. In this example, the endovascular robotic system comprises a first endovascular robotic instrument located at the first location and a second endovascular robotic instrument located at a second location which is different from the first location. The first endovascular robotic instrument is communicatively coupled with the second endovascular robotic instrument, wherein a first functioning of the first endovascular robotic instrument is identical to a second functioning of the second endovascular robotic instrument.

At step S904, the method comprises driving the second endovascular robotic instrument. Driving the second endovascular robotic instrument may be performed by a surgeon located at the second location.

At step S906, the method 900 comprises generating haptic feedback data with a second haptic feedback unit of the second endovascular robotic instrument.

At step S908, haptic feedback data is sent from the second endovascular robotic instrument to the first endovascular robotic instrument.

At step S910, the method 900 comprises mimicking, by the first endovascular robotic instrument and based on the haptic feedback data received at step S908, movement of the second endovascular robotic instrument.

The method 800 may be combined with the method 900. In other words, haptic feedback data may be generated in both of the first endovascular robotic instrument and the second endovascular robotic instrument using respective sensors, and haptic feedback data may be sent from the first endovascular robotic instrument to the second endovascular robotic instrument and vice versa in order to equalize forces acting on the sensors by driving one or both of the first endovascular robotic instrument and the second endovascular robotic instrument. In some examples, one force is higher than another force by a predefined factor.

Example implementations of the endovascular robotic system and method(s) as described herein allow in particular for using haptic feedback for navigating in particular a guide wire and/or a catheter remotely, having a virtual cut of the guide wire and/or the catheter, while feeling as if the guide wire and the catheter is continuous from the endovascular robotic instrument which can be operated by a surgeon at a second location to another endovascular robotic instrument arranged at the first location and used for performing surgery on a patient. Linear and rotational force balance sensing may be used, in particular based on a master-slave concept where the master and slave devices (and/or sensors) may be changed in real time according to force bal-ancing from sensor readings.

Example implementations of the system and method(s) as described herein may equally be used for a vascular robotic system comprising first and second vascular robotic instruments.

In some examples, a signal (which may relate, for example, to a feedback signal and/or an optical signal and/or vibration) may be transmitted by the first endovascular robotic instrument and/or second endovascular robotic instrument to a further device (which may in some examples be part of the endovascular robotic system), such as a monitor. This further device may allow for remote controlling (using, for example, a monitor and a remote controller) of one or both of the first and second endovascular robotic instruments and/or other parts of the endovascular robotic system. In some examples, images may be sent by the first and/or second endovascular robotic instruments to the further device.

The further device may comprise one or more components. In some examples, monitors are arranged in the operating room and/or in a control room used to control the first and/or second endovascular robotic instruments and/or in an auditorium.

In some examples, the endovascular robotic instrument which is arranged at the patient side/location may comprise a sterility function/sterility application device, which may, in some examples, not need to be provided at the physician side.

In some examples, the table on which the patient can be put may provide for a functional attachment of the patient to the table. This functional attachment may, in some examples, not need to be provided at the table arranged at the physician side/location.

If a certain function may be provided only for the first endovascular robotic instrument or the second endovascular robotic instrument but not the other one of the endovascular robotic instruments (for example, as outlined above, a sterility function and/or a functional attachment may be provided only at the patient side/location), different software and/or hardware may be provided (at least for components which differ between the endovascular robotic instruments) for the different endovascular robotic instruments.

No doubt many other effective alternatives will occur to the skilled person. It will be understood that the invention is not limited to the described embodiments and en-compasses modifications apparent to those skilled in the art and lying within the scope of the claims appended hereto.

The invention claimed is:

1. An endovascular robotic system, comprising:
a first endovascular robotic instrument located at a first location, and
a second endovascular robotic instrument located at a second location different from the first location,
wherein the first endovascular robotic instrument is com-municatively coupled with the second endovascular robotic instrument, wherein a first functioning of the first endovascular robotic instrument is identical to a second functioning of the second endovascular robotic instrument,
wherein the first endovascular robotic instrument com-prises a first haptic feedback unit configured to generate first haptic feedback data dependent on a first move-ment, for implementing the first functioning, of the first endovascular robotic instrument,
wherein the first endovascular robotic instrument is con-figured to send the first haptic feedback data to the second endovascular robotic instrument, and
wherein the second endovascular robotic instrument is configured to mimic, for implementing the second functioning, the first movement of the first endovascu-lar robotic instrument based on the first haptic feedback data received from the first endovascular robotic instru-ment.

2. The endovascular robotic system as claimed in claim 1, wherein the second endovascular robotic instrument com-prises a second haptic feedback unit configured to generate second haptic feedback data dependent on a second move-ment, for implementing the second functioning, of the second endovascular robotic instrument,
wherein the second endovascular robotic instrument is configured to send the second haptic feedback data to the first endovascular robotic instrument, and
wherein the first endovascular robotic instrument is con-figured to mimic, for implementing the first function-ing, the second movement of the second endovascular robotic instrument based on the second haptic feedback data received from the second endovascular robotic instrument.

3. The endovascular robotic system as claimed in claim 1, wherein the first endovascular robotic instrument comprises one or more first endovascular robotic instrument compo-nents, wherein the second endovascular robotic instrument comprises one or more second endovascular robotic instru-ment components, and wherein one of said first endovascu-lar robotic instrument components is identical to a corre-sponding, respective one of said second endovascular robotic instrument components.

4. The endovascular robotic system as claimed in claim 3, wherein said mimicking a said movement of a said endo-vascular robotic instrument comprises driving a said endo-vascular robotic instrument component.

5. The endovascular robotic system as claimed in claim 4, wherein the system further comprises:
a drive unit provided on the second endovascular robotic instrument via which the one or more second endovas-cular robotic instrument components are driven based on the first haptic feedback data.

6. The endovascular robotic system as claimed in claim 1, wherein the first endovascular robotic instrument comprises a first medical device and wherein the second endovascular robotic instrument comprises a second medical device.

7. The endovascular robotic system as claimed in claim 1, further comprising:
an optical detection unit arranged at the first location, and
a visualization unit arranged at the second location,
wherein the optical detection unit is configured to opti-cally detect said first movement, generate, based on said optical detection of said first movement, move-ment data and send said movement data to the visual-ization unit, and
wherein the visualization unit is configured to visualize, based on the movement data, said first movement.

8. The endovascular robotic system as claimed in claim 7, wherein the visualization unit is configured to visualize at least a part of the first endovascular robotic instrument as a virtual extension of at least a part of the second endovascular robotic instrument.

9. The endovascular robotic system as claimed in claim 1, wherein the first haptic feedback unit comprises a first linear force sensor configured to sense a first linear force acting on the first endovascular robotic instrument and/or a first rotational force sensor configured to sense a first rotational force acting on the first endovascular robotic instrument.

10. The endovascular robotic system as claimed in claim 9, wherein a said sensor is configured to:

move linearly and/or rotationally together with a corresponding, respective said endovascular robotic instrument, and create an increased and/or decreased force to said corresponding, respective endovascular robotic instrument during said linear and/or rotational movement together with said corresponding, respective endovascular robotic instrument.

11. The endovascular robotic system as claimed in claim 1, wherein the second endovascular robotic instrument comprises a second haptic feedback unit configured to generate second haptic feedback data dependent on a second movement, for implementing the second functioning, of the second endovascular robotic instrument, wherein the second endovascular robotic instrument is configured to send the second haptic feedback data to the first endovascular robotic instrument, wherein the first endovascular robotic instrument is configured to mimic, for implementing the first functioning, the second movement of the second endovascular robotic instrument based on the second haptic feedback data received from the second endovascular robotic instrument, and wherein the second haptic feedback unit comprises a second linear force sensor configured to sense a second linear force acting on the second endovascular robotic instrument and/or a second rotational force sensor configured to sense a second rotational force acting on the second endovascular robotic instrument.

12. The endovascular robotic system as claimed in claim 1, wherein the second endovascular robotic instrument comprises a second haptic feedback unit configured to generate second haptic feedback data dependent on a second movement, for implementing the second functioning, of the second endovascular robotic instrument, wherein the second endovascular robotic instrument is configured to send the second haptic feedback data to the first endovascular robotic instrument, and wherein the first endovascular robotic instrument is configured to mimic, for implementing the first functioning, the second movement of the second endovascular robotic instrument based on the second haptic feedback data received from the second endovascular robotic instrument, wherein the first haptic feedback unit comprises a first linear force sensor configured to sense a first linear force acting on the first endovascular robotic instrument and/or a first rotational force sensor configured to sense a first rotational force acting on the first endovascular robotic instrument, wherein the second haptic feedback unit comprises a second linear force sensor configured to sense a second linear force acting on the second endovascular robotic instrument and/or a second rotational force sensor configured to sense a second rotational force acting on the second endovascular robotic instrument, and wherein the endovascular robotic system is configured to:

determine a relative force between (i) the first linear force and the second linear force, and/or (ii) the first rotational force and the second rotational force, and drive the first endovascular robotic instrument and/or the second endovascular robotic instrument to (i) adjust the first linear force to be equal to the second linear force and/or adjust the second linear force to be equal to the first linear force, and/or (ii) adjust the first rotational force to be equal to the second rotational force and/or adjust the second rotational force to be equal to the first rotational force.

13. The endovascular robotic system as claimed in claim 12, wherein the endovascular robotic system is further configured to determine, based on sensor readings of (i) the first linear force sensor and the second linear force sensor, and/or (ii) the first rotational force sensor and the second rotational force sensor, (i) whether to adjust the first linear force to be equal to the second linear force and/or adjust the second linear force to be equal to the first linear force, and/or (ii) whether to adjust the first rotational force to be equal to the second rotational force and/or adjust the second rotational force to be equal to the first rotational force.

14. The endovascular robotic system as claimed in claim 1, wherein the first endovascular robotic instrument comprises first rotational and axial motor gears for driving the first endovascular robotic instrument axially and rotationally, wherein the second endovascular robotic instrument comprises second rotational and axial motor gears for driving the second endovascular robotic instrument axially and rotationally, and wherein the first rotational and axial motor gears are identical to the second rotational and axial motor gears.

15. The endovascular robotic system as claimed in claim 1, further comprising a data store adapted to store said haptic feedback data, wherein the endovascular robotic system is configured to:

retrieve said haptic feedback data from the data store, and drive the first endovascular robotic instrument to perform said first functioning and/or drive the second endovascular robotic instrument to perform said second functioning.

16. The endovascular robotic system as claimed in claim 1, wherein said communicative coupling of the first endovascular robotic instrument with the second endovascular robotic instrument comprises a wireless communicative coupling.

17. The endovascular robotic system as claimed in claim 1, further comprising one or more controls, wherein the one or more controls are configured to indicate a status of the endovascular robotic system and output a signal dependent on the status of the endovascular robotic system.

18. The endovascular robotic system as claimed in claim 17, wherein the status comprises a value of a force applied to one or both of the first and second endovascular robotic instruments, and wherein the signal is output if the force is above or below a threshold force.

19. A medical intervention system, comprising:

a first medical instrument located at a first location, and a second medical instrument located at a second location different from the first location, wherein the first medical instrument is communicatively coupled with the second medical instrument, wherein the first medical instrument is configured to perform a first type of intervention on a patient, wherein the second medical instrument is configured to perform a second type of intervention on a patient, wherein the first type and the second type are identical or substantially identical types of intervention, wherein the first medical instrument comprises a first haptic feedback unit configured to generate first haptic feedback data dependent on a first movement of the first medical instrument, wherein the first medical instrument is configured to send the first haptic feedback data to the second medical instrument, and wherein the second medical instrument is configured to mimic the first movement of the first medical instrument based on the first haptic feedback data received from the first medical instrument.

20. A method for intervention on a patient, the method comprising:

providing an endovascular robotic system comprising:

a first endovascular robotic instrument located at a first location, and a second endovascular robotic instrument located at a second location different from the first location, wherein the first endovascular robotic instrument is communicatively coupled with the second endovascular robotic instrument, wherein a first functioning of the first endovascular robotic instrument is identical to a second functioning of the second endovascular robotic instrument, wherein the first endovascular robotic instrument comprises a first haptic feedback unit configured to generate first haptic feedback data dependent on a first movement, for implementing the first functioning, of the first endovascular robotic instrument, wherein the first endovascular robotic instrument is configured to send the first haptic feedback data to the second endovascular robotic instrument, and wherein the second endovascular robotic instrument is configured to mimic, for implementing the second functioning, the first movement of the first endovascular robotic instrument based on the first haptic feedback data received from the first endovascular robotic instrument;

operating the second endovascular robotic instrument; and triggering movement of the first endovascular robotic instrument to mimic said operating of the second endovascular robotic instrument.

* * * * *